United States Patent
Miwa et al.

(10) Patent No.: US 8,084,003 B2
(45) Date of Patent: Dec. 27, 2011

(54) OZONE DETECTING DEVICE

(75) Inventors: Takashi Miwa, Kanagawa (JP); Yasuko Maruo, Kanagawa (JP); Jiro Nakamura, Kanagawa (JP); Tatsuya Kunioka, Kanagawa (JP); Seizo Sakata, Kanagawa (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 183 days.

(21) Appl. No.: 12/444,845

(22) PCT Filed: Oct. 17, 2007

(86) PCT No.: PCT/JP2007/070260
§ 371 (c)(1),
(2), (4) Date: Apr. 8, 2009

(87) PCT Pub. No.: WO2008/056513
PCT Pub. Date: May 15, 2008

(65) Prior Publication Data
US 2010/0074800 A1    Mar. 25, 2010

(30) Foreign Application Priority Data
Nov. 7, 2006    (JP) .................... 2006-301353

(51) Int. Cl.
*G01N 33/52* (2006.01)
(52) U.S. Cl. ........... 422/420; 422/86; 422/87; 422/400; 422/401; 436/135
(58) Field of Classification Search ............ 422/56, 422/86, 87, 400, 401, 420; 436/135
See application file for complete search history.

(56) References Cited

U.S. PATENT DOCUMENTS

| | | | | |
|---|---|---|---|---|
| 6,117,685 | A * | 9/2000 | Omatsu et al. | 436/135 |
| 6,852,281 | B2 * | 2/2005 | Inoue et al. | 422/58 |
| 7,662,636 | B2 * | 2/2010 | Maruo et al. | 436/135 |
| 2004/0229372 | A1 * | 11/2004 | Omatsu et al. | 436/135 |

FOREIGN PATENT DOCUMENTS

| | | | |
|---|---|---|---|
| EP | 0275719 | * | 7/1988 |
| EP | 1163913 A2 | | 12/2001 |

(Continued)

OTHER PUBLICATIONS

Flanklin et al., "Ozone Measurement in South Carolina Using Passive Sampler", Journal of the Air & Waste Measurement Association, vol. 54, pp. 1312-1320, 2004.
"Operating Instructions for Ozone Monitor", Part#380010-10, http://www.Kandmenvironmental.com/PDFs/ozone.pdf.
Ito, "Mysteries of Ozone".
Minami et al., "Application of Ferulic Acid for Cosmetics", Fragr.J., 1992, vol. 20, No. 4, pp. 89-93.

(Continued)

*Primary Examiner* — Jill Warden
*Assistant Examiner* — Monique Cole
(74) *Attorney, Agent, or Firm* — Blakely, Sokoloff, Taylor & Zafman (57) ABSTRACT

A vessel (102) containing a detector solution (101) is prepared. The detector solution (101) is an aqueous solution prepared by dissolving a detector component containing a dye which changes its color when reacting with ozone gas, a humectant, and an ultraviolet absorber having a hydrophilic group. A prepared sheet-like carrier (103) is dipped in the detector solution (101) for, e.g., 30 sec, thereby forming an impregnated sheet (104) by impregnating the sheet-like carrier (103) with the detector solution (101). The impregnated sheet (104) is then dried by evaporating the solvent (medium) such as water contained in the impregnated sheet (104), thereby forming a sheet-like ozone detecting device (105).

8 Claims, 5 Drawing Sheets

FOREIGN PATENT DOCUMENTS

| | | |
|---|---|---|
| JP | 07-012733 A | 1/1995 |
| JP | 2000-111541 A | 4/2000 |
| JP | 2000-515590 A | 8/2000 |
| JP | 3257622 B | 12/2001 |
| JP | 2004-144729 A | 5/2004 |
| JP | 2005-156220 A | 6/2005 |
| WO | WO 2006/016623 A1 | 2/2006 |

OTHER PUBLICATIONS

Lyng et al., "Bixin and α—cyclodextrin inclusion complex and stability tests", Process Biochem., 2005, vol. 40, pp. 865-872.

Pan et al., "UV-VIS. Spectroscopic characteristics of ferulic acid and related compounds", J. Wood Chem. Technol., 2002, vol. 22, No. 2/3, pp. 137-146.

* cited by examiner

OZONE DETECTING DEVICE

The present patent application is a non-provisional application of International Application No. PCT/JP2007/070260, filed Oct. 17, 2007.

TECHNICAL FIELD

The present invention relates to an ozone detecting device for detecting ozone existing in a gas such as the air.

BACKGROUND ART

Presently, $NO_x$, SPM (Suspended Particulate Matter), and photochemical oxidant cause air pollution, and the influence on the environment is regarded as a problem. For example, the photochemical oxidant mainly containing a strongly oxidizing substance such as ozone is produced by a photochemical reaction of a pollutant such as $NO_x$ or hydrocarbon exhausted from factories, offices, and automobiles when the pollutant is irradiated with the sunlight, and causes photochemical smog.

The photochemical oxidant is almost made of ozone, and measurement stations in various places measure the concentration of ozone by an automatic measurement method such as an ultraviolet absorption method. Ozone gas concentration measurement performed by this automatic measurement method can measure a slight amount of a gas, i.e., a few ppb of a gas, but the measurement is expensive and requires constant setup in order to maintain the accuracy. Also, in automatic measurements performed by these apparatuses, electric power is always necessary, and maintenance and management are essential, so enormous costs are required. In addition, temperature-controlled installation environments and standard gases for calibration must be secured for these measurements.

To accurately investigate the gas concentration distribution in an environment and evaluate the influence on a local environment, it is necessary to increase the number of observation points and perform measurement and investigation on a nationwide scale. However, it is very difficult to perform the above-mentioned automatic measurement method in many observation points. Therefore, demands have arisen for a readily usable, compact, inexpensive ozone gas analyzer and a simple measurement method.

Recently, ozone is attracting attention because it has strong sterilizing power (oxidizing power), and changes into oxygen and produces no harmful substance after decomposition. This is extending the use of ozone to various industrial fields such as water processing, food sterilization, and paper bleaching. Accordingly, reference values of 100 ppb and 8 hrs are set for the ozone concentration as labor environmental standards. In a factory using ozone, it is necessary not only to install ozone alarms, but also to manage the state in which each worker works within the range of the labor standards. This requires a measurement device that can be carried by a worker.

Under these circumstances, ozone gas measurement techniques have been presently extensively developed. Examples are a semiconductor gas sensor, solid-state electrolyte gas sensor, electrochemical gas sensor, and quartz oscillating gas sensor. However, these sensors have been developed to evaluate short-time responses, and only a few sensors have been developed for monitoring requiring measurement data accumulation. When it is necessary to accumulate measurement data, therefore, the sensors must always be operated. Also, a sensing unit of, e.g., the semiconductor sensor must be held at a few hundred ° C., so a large amount of electric power is always necessary to constantly operate the sensor.

Furthermore, the above-mentioned sensors have a sensitivity of about sub-ppm, and hence cannot measure concentrations in real environments, e.g., cannot measure 10 ppb of ozone. Although some semiconductor sensors react to 10 ppb of ozone, the sensor output is nonlinear with respect to the concentration, and the output value largely changes from one sensor to another. This makes comparison difficult when using different sensors. Also, the influence of another gas cannot be neglected in many cases.

There is also a method using a detector tube type gas measurement device. Unfortunately, this method has also been developed to locally measure a very-short-time concentration in a measurement point. This makes it difficult to obtain long-term cumulative measurement data. In addition, this method using a detector tube requires the presence of an operator in a measurement site, and also poses the measurement accuracy problem that different operators read color changes between measurements differently.

On the other hand, ozone detecting paper carrying starch and potassium iodide has been proposed as a simple, high-sensitivity ozone analyzing technique (see reference 1: Japanese Patent No. 3257622). However, this technique disclosed in reference 1 requires a pump for forcedly drawing a gas to be detected, a light source for measurement, and electric power for driving a detector including the pump and light source. Also, a special sheet-like carrier is necessary and must be replaced whenever measurement is performed. This makes cumulative measurement difficult. In addition, the measurement using the detecting paper described above detects all photochemical oxidants instead of ozone.

As another simple, high-sensitivity ozone gas analyzing method, a technique using ozone detecting paper carrying indigo carmine has been proposed (see reference 2: Anna C. Franklin, et al., "Ozone Measurement in South Carolina Using Passive Sampler", Journal of the Air & Waste Measurement Association, Vol. 54, pp. 1312-1320, 2004). A technique by which a membrane filter is placed on the surface of an ozone detecting sheet carrying a blue indigo dye, and the sensitivity is controlled by adjusting the thickness of the membrane filter has also been proposed (see reference 3: "Operating Instructions for Ozone Monitor", Part #380010-10, http://www.kandmenvironmental.com/PDFs/ozone.pdf).

DISCLOSURE OF INVENTION

Problems to be Solved by the Invention

Unfortunately, the technique of reference 1 is expensive because the pump and optical system are necessary, and the techniques of references 2 and 3 have the problem in outdoor use under the sunshine. In the conventional techniques of references 2 and 3, the cumulative concentration of ozone gas can be measured by the change in color of the ozone detecting paper or detecting device. Under the sunlight in outdoor use, however, the color changes even if there is no ozone gas. The cause of this problem is ultraviolet light contained in the sunlight. As described above, the technique of reference 1 has the problem that the apparatus cost is high, and the techniques of references 2 and 3 have the problem that ozone gas measurement is limited to the indoors, and outdoor measurement such as the detection of ozone caused by photochemical smog is not easy. Also, even when ozone is generated by using ultraviolet light, these conventional techniques cannot easily measure the generated ozone gas.

The present invention has been made to solve the problems as described above, and has as its object to provide an ozone detecting device capable of simply detecting the cumulative amount, from the start of measurement, of ozone in a gas to be measured, and accurately detecting ozone even under ultraviolet radiation.

Means for Solving the Problems

An ozone detecting device according to the present invention includes at least a carrier made of fibers, a detector component carried by the carrier and containing a dye which changes a color when reacting with ozone gas, and an ultraviolet absorber carried by the carrier and having a hydrophilic group. The ultraviolet absorber carried together with the dye by the carrier absorbs ultraviolet light irradiating the carrier.

Effect of the Invention

In the present invention as explained above, the carrier carries the ultraviolet absorber together with the detector component, so the ultraviolet absorber carried by the carrier carrying the dye absorbs ultraviolet light irradiating the carrier.

Consequently, the present invention achieves a remarkable effect, i.e., can provide an ozone detecting device capable of simply detecting the cumulative amount of ozone in a gas to be measured, and accurately detecting ozone even under ultraviolet radiation.

BEST MODE FOR CARRYING OUT THE INVENTION

Figure 1A:
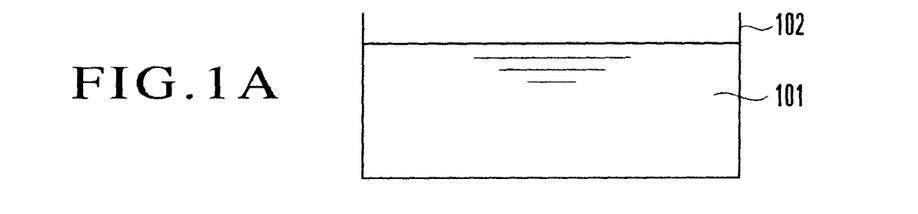
FIGS. 1A to 1E are views of steps for explaining an example of an ozone detecting device manufacturing method according to an embodiment of the present invention.

An embodiment of the present invention will be explained below with reference to the accompanying drawings. FIGS. 1A to 1E are views of steps for explaining an example of an ozone detecting device manufacturing method according to the embodiment of the present invention. First, as shown in FIG. 1A, a vessel 102 containing a detector solution 101 is prepared. The detector solution 101 is an aqueous solution prepared by dissolving a detector component containing a dye that changes its color (light absorption spectrum) when reacting with ozone gas, a humectant, and an ultraviolet absorber having a hydrophilic group.

As the dye, it is possible to apply, e.g., dyes having an indigo ring such as indigo carmine ($C_{16}H_8N_2Na_2O_8S_2$) and indigo. These dyes are used as they are acidified by an acidic substance such as citric acid. When using indigo carmine or the like as the dye in this embodiment, therefore, the dye and acidic substance form the detector component. When the dye having an indigo ring reacts with ozone, a C=C bond contained in the molecular skeleton decomposes. Since this changes the structure and electron state of the dye molecule, light absorption in the visible region changes, and the color (hue) changes (fades). Note that although the acidic substance does not directly react with ozone, it is contained in the detector component as a component participating in the reaction between the dye and ozone gas.

It is also possible to apply azo dyes such as chalcone ($HOC_{10}H_6N:NC_{10}H_5(OH)SO_3Na$), Acid Alizarin Violet N (also called Acid Chrome Violet K: $C_{16}H_{11}N_2NaO_5S$), Orange I ($C_{16}H_{11}N_2NaO_4S$), and methyl orange ($C_{14}H_{14}N_3NaO_3S$). When the azo dye reacts with ozone, an azo group (N=N double bond) contained in the molecular skeleton decomposes (oxidizes). Since this changes the structure and electron state of the dye molecule, light absorption in the visible region changes, and the color changes.

Furthermore, it is possible to apply anthraquinone-based dyes having a hydroxy group such as alizarin ($C_{14}H_{10}O_2(OH)_2$) and Alizarin Red S (9,10-dihydro-3,4-dihydroxy-9,10-dioxo-2-anthracenesulfonic acid, sodium salt: $C_{14}H_{10}O_2(OH)_2SO_3Na$). These dyes are used as they are alkalized by an alkaline substance such as sodium hydroxide. When using alizarin or the like as the dye, therefore, the dye and alkaline substance form the detector component. When the anthraquinone-based dye having a hydroxy group (—OH) reacts with ozone, a C=O double bond contained in the molecular skeleton decomposes. Since this changes the structure and electron state of the dye molecule, light absorption in the visible region changes, and the color changes.

A dye having a polyene structure such as bixin or norbixin, e.g., an annatto dye, may also be applied. When the dye having the polyene structure reacts with ozone, a C=C bond contained in the molecular skeleton decomposes. Since this changes the structure and electron state of the dye molecule, light absorption in the visible region changes, and the color changes.

As the humectant, it is possible to apply, e.g., glycerin ($C_3H_8O_3$), ethyleneglycol ($C_2H_6O_2$), and propyleneglycol ($C_3H_8O_2$).

As the ultraviolet absorber having a hydrophilic group, it is possible to apply, e.g., 2-hydroxy-4-methoxybenzophenone-5-sulfonic acid, 2-hydroxy-4-methoxybenzophenone-5-sodium sulfonate, and ferulic acid (4-hydroxy-3-methoxy cinnamic acid). All these ultraviolet absorbers have a benzene ring in the skeleton. When using ferulic acid, as will be described later, an ozone detecting device containing the ultraviolet absorber is manufactured by first forming an ozone detecting device containing no ultraviolet absorber, dipping the ozone detecting device in an acetone solution of ferulic acid, and drying the ozone detecting device. Therefore, ferulic acid makes the manufacture more difficult than when using a water-soluble ultraviolet absorber. As is well known, however, ferulic acid has high safety because it is a substance contained in rice bran and the like.

For example, the detector solution 101 is prepared by adding pure water to 0.045 g of indigo carmine, 0.8 g of 2-hydroxy-4-methoxybenzophenone-5-sulfonic acid trihydrate, and 12.5 g of glycerin to make 50 ml as a whole. Indigo carmine is a dye having an indigo ring, and the color of the acidified detector solution 101 is blue. Note that indigo carmine is used as it is acidified, citric acid or acetic acid is generally added. In the above composition, however, indigo carmine is acidified by using 2-hydroxy-4-methoxybenzophenone-5-sulfonic acid, so no other acidic substance such as citric acid is added.

Figure 1B:
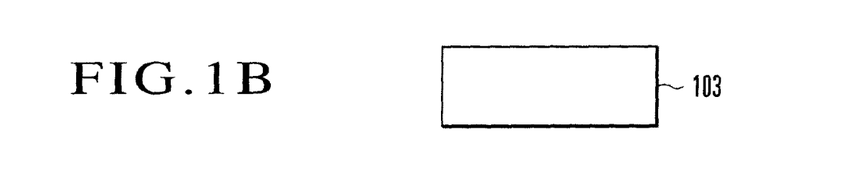

Then, as shown in FIG. 1B, a carrier 103 having predetermined dimensions is prepared. The carrier 103 is a sheet made of fibers such as cellulose. An example is cellulose filter paper (No. 2) manufactured by ADVANTEC (TOYO FILTER PAPER). The color of the carrier 103 can be, e.g., white. Note that the carrier 103 is not limited to a sheet and may also have another shape. For example, the carrier 103 may also be a plate. As will be described below, the carrier 103 need only be impregnated with the detector solution 101, and carry the dye, ultraviolet absorber, and the like such that they can contact a gas to be detected.

Figure 1C:
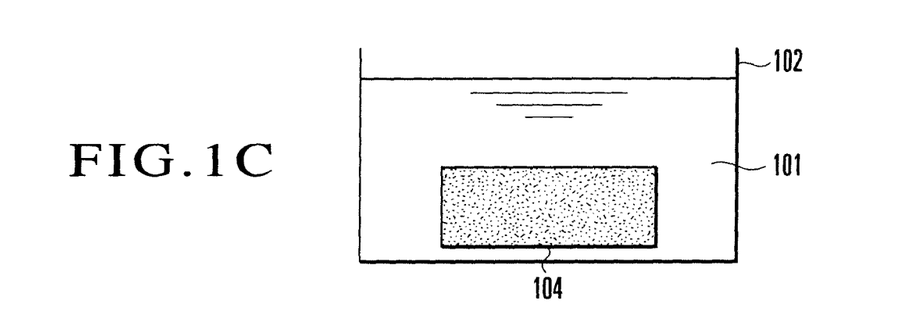

Subsequently, the prepared carrier 103 is dipped in the detector solution 101 for, e.g., 30 sec so as to impregnate the carrier 103 with the detector solution 101, thereby forming an impregnated carrier 104 impregnated with the detector solution 101 as shown in FIG. 1C.

Figure 1D:
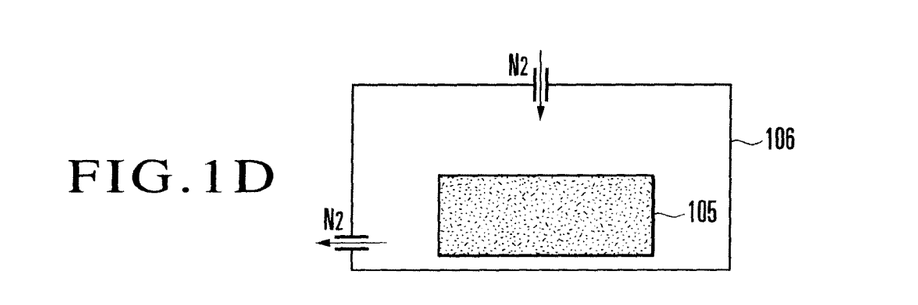

After that, the impregnated carrier 104 is pulled up from the detector solution 101, and dried with air. After being dried with air to some extent, the impregnated carrier 104 is dried in dry nitrogen by evaporating the solvent (medium) such as water contained in the impregnated carrier 104. For example, as shown in FIG. 1D, the impregnated carrier 104 is placed in a nitrogen gas stream in a predetermined vessel 106 filled with circulating nitrogen gas, and dried by holding this state for 24 hrs or more, thereby forming a sheet-like ozone detecting device 105.

Figure 1E:
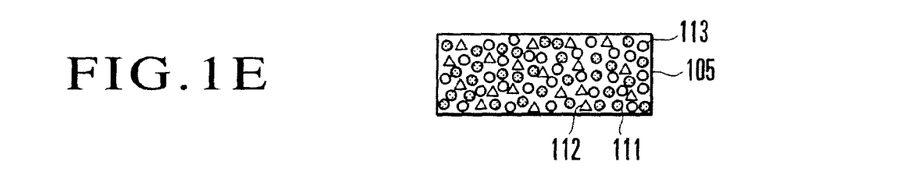

As shown in FIG. 1E, the ozone detecting device 105 thus formed carries a dye 111, ultraviolet absorber 112, and humectant 113. In this example, indigo carmine is used as the dye 111, and the obtained ozone detecting device 105 has the color of the dye 111. It is readily possible to visually confirm this color. Note that "carry" mentioned above indicates a state in which substances such as a dye, ultraviolet absorber, and humectant chemically, physically, or electrically combine with a carrier (substrate), e.g., a state in which a sheet made of fibers such as cellulose is coated and/or impregnated with a dye.

When the ozone detecting device 105 manufactured as described above is exposed to an environment in which ozone exists, the density of the color of the dye gradually decreases with the elapse of the exposure time, and the color finally changes to white. For example, the color changes to slightly yellowish white when the ozone detecting device 105 is exposed to an environment in which the ozone concentration is 0.04 ppm for 24 hrs. Note that when another dye is used, the color almost disappears and the original color (white) of the filer paper appears in some cases.

As described above, the ozone detecting device 105 can detect ozone by the change of color, and can perform cumulative detection, i.e., can measure the cumulative amount from the start of measurement. This color change is presumably discoloration corresponding to the decomposition of the dye 111 by ozone. Note that the color of the carrier 103 is white in the above description, but the present invention is not limited to this, and the carrier 103 need only have a color whose absorption wavelength in the visible region does not overlap the color of a dye used. For example, a yellowed carrier (filter paper) can be used when using indigo carmine. In this case, a detecting device is colored green, and changes its color to yellow when reacting with ozone.

Also, the ozone detecting device 105 is impregnated with the detector solution 101 containing about 20 wt % of the humectant, and hence carriers the humectant 113. This more effectively achieves the above-mentioned color change (ozone detecting capability) caused by the existence of ozone. This is so probably because the humectant 113 contained in the ozone detecting device 105 accelerates the discoloration reaction of the dye in the ozone detecting device 105 caused by ozone. However, if the concentration of the humectant in the detector solution is too high, e.g., exceeds 50%, the time required for drying becomes enormous, and this makes it difficult to manufacture a detecting device having high reproducibility.

In addition, since the ozone detecting device 105 contains the ultraviolet absorber 112, the influence of ultraviolet radiation is suppressed. For example, when using no ultraviolet absorber, the color of an ozone detecting device changes when the device is exposed to the sunshine even if there is no ozone. This phenomenon is particularly significant when an ozone detecting device is manufactured using a humectant. In this case, the color change can be visually confirmed when the device is exposed to the sunlight for about ten to a few ten min, even if there is no ozone. Thus, an ozone detecting device using no ultraviolet absorber is incapable of ozone detection in an environment in which the device is exposed to ultraviolet radiation. By contrast, even when the ozone detecting device 105 is exposed to the sunlight for about ten to a few ten min, the influence of ultraviolet radiation is reduced to such an extent that no discoloration is visually confirmed, so the ozone detecting device 105 can detect ozone even in an environment in which it is exposed to ultraviolet radiation.

The influence of ultraviolet radiation when using the humectant described above will be explained below. First, the use of the humectant presumably allows the carrier to carry the dye together with water. If ozone existing in the atmosphere acts on (dissolves in) the carrier, a highly reactive hydroxy radical or hydroperoxy radical is perhaps generated in the water carried together with the dye (reference 4: Tairo Ito, "Mysteries of Ozone"). Since these radicals exhibit high oxidizing power, the radical generated as described above probably decomposes the dye. On the other hand, when the carrier carrying the water together with the dye is irradiated with ultraviolet light, a highly reactive oxygen radical is presumably generated in the water and decomposes the dye in the same manner as when ozone acts. This perhaps poses the problem of ultraviolet radiation described previously.

Figure 2:
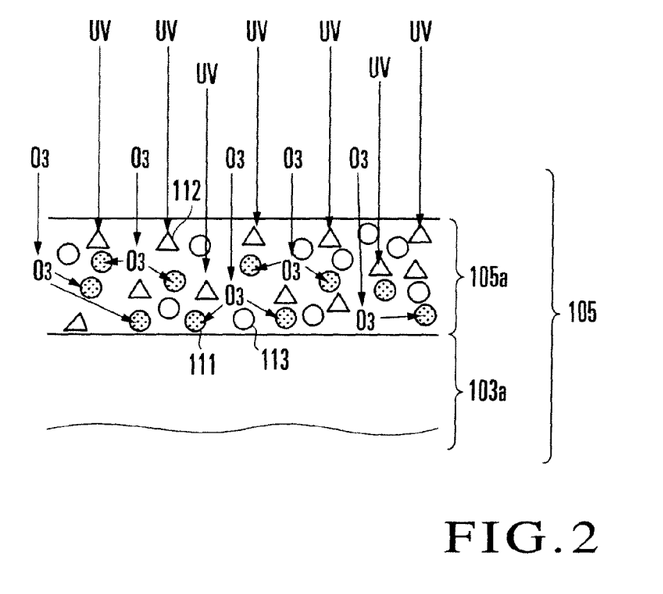
FIG. 2 is a view for explaining the action of an ultraviolet absorber.

A case in which, as shown in FIG. 2, the ozone detecting device 105 carrying the ultraviolet absorber 112 is irradiated with ultraviolet light and ozone acts on the ozone detecting device 105 will be explained below. In the ozone detecting device 105, a water layer 105a is formed by the effect of the humectant 113 on the surface of fibers 103a forming a unit, and the ultraviolet absorber 112 presumably exists together with the dye 111 in the water layer 105a. Since ultraviolet (UV) light linearly enters, the ultraviolet absorber 112 converts most of the ultraviolet light into heat and the like near the surface of the water layer 105a. This significantly reduces, e.g., the generation of an oxygen radical contributing to the decomposition of the dye 111 and the direct decomposition of the dye caused by the ultraviolet light.

By contrast, since ozone ($O_3$) is a gas, ozone dissolves and diffuses in the water layer 105a even when the ultraviolet absorber 112 exists. Also, the reactions such as oxidation and decomposition of the ultraviolet absorber 112 hardly consume ozone. Therefore, most ozone probably dissolves and diffuses in the water layer 105a and acts on the dye 111 as described above, thereby decomposing the dye 111. Accordingly, when a predetermined amount of the ultraviolet absorber 112 exists on the surface of the water layer 105a, it is possible to suppress the entrance of ultraviolet light and the decomposition of the dye 111 by ultraviolet light while ozone can enter.

The effect of the ultraviolet absorber will be explained in more detail below. First, detector solution A is prepared by dissolving 0.045 g of indigo carmine, 3.0 g of citric acid, and 12.5 g of glycerin in water to make 50 ml as a total amount, and ozone detecting device A is manufactured following the same procedures as described above by using detector solution A. Ozone detecting device A is a sample containing no ultraviolet absorber. The color of ozone detecting device A thus formed is blue.

Then, detector solution B is prepared by dissolving 0.045 g of indigo carmine, 0.8 g of 2-hydroxy-4-methoxybenzophenone-5-sulfonic acid trihydrate, and 12.5 g of glycerin in water to make 50 ml as a total amount, and ozone detecting device B is manufactured following the same procedures as described above by using detector solution B. The color of ozone detecting device B thus formed is blue.

Detector solution C is prepared by dissolving 0.045 g of indigo carmine, 1.0 g of 2-hydroxy-4-methoxybenzophenone-5-sodium sulfonate, 3.5 g of citric acid, and 12.5 g of glycerin in water to make 50 ml as a total amount, and ozone detecting device C is manufactured following the same procedures as described above by using detector solution C. The color of ozone detecting device C thus formed is blue. Note that 2-hydroxy-4-methoxybenzophenone-5-sodium sulfonate is obtained by dissolving equal molar quantities of 2-hydroxy-4-methoxybenzophenone-5-sulfonic acid trihydrate and sodium hydroxide in water, and drying the aqueous solution.

A detector solution is prepared by dissolving 0.045 g of indigo carmine, 3.0 g of citric acid, and 12.5 g of glycerin in water to make 50 ml as a total amount, and an ozone detecting device is manufactured following the same procedures as described above by using this detector solution. The detector solution is identical to detector solution A described above, and the ozone detecting device is also identical to ozone detecting device A described above. Then, an ultraviolet absorber solution is prepared by dissolving 3.5 g of ferulic acid in 50 ml of acetone, and the above-mentioned ozone detecting device is dipped in this ultraviolet absorber solution for 10 sec so as to be impregnated with the ultraviolet absorber solution, thereby forming ozone detecting device D impregnated with the ultraviolet absorber solution.

After that, ozone detecting device D is pulled up from the ultraviolet absorber solution and dried with air. After being dried to some extent, ozone detecting device D is dried in dry nitrogen by evaporating the solvent (medium) such as water contained in ozone detecting device D. For example, as shown in FIG. 1D, ozone detecting device D is dried as it is placed in a nitrogen gas stream inside the predetermined vessel 106 filled with circulating nitrogen gas, and held in this state for 24 hrs or more.

Next, samples using an ultraviolet absorber insoluble in water will be explained below as comparative samples.

First, a detector solution is prepared by dissolving 0.045 g of indigo carmine, 3.0 g of citric acid, and 12.5 g of glycerin in water to make 50 ml as a total amount, and an ozone detecting device is manufactured following the same procedures as described above by using this detector solution. The detector solution is identical to detector solution A described earlier, and the prepared ozone detecting device is also identical to ozone detecting device A described earlier.

Then, an ultraviolet absorber solution is prepared by dissolving 0.5 g of 4-dodecyloxy-2-hydroxybenzophenone in 50 ml of acetone, and the above-mentioned ozone detecting device is dipped in this ultraviolet absorber solution for 10 sec so as to be impregnated with the ultraviolet absorber solution, thereby forming ozone detecting device E impregnated with the ultraviolet absorber solution. After that, ozone detecting device E is pulled up from the ultraviolet absorber solution and dried in the same manner as described above.

A detector solution is prepared by dissolving 0.045 g of indigo carmine, 3.0 g of citric acid, and 12.5 g of glycerin in water to make 50 ml as a total amount, and an ozone detecting device is manufactured following the same procedures as described above by using this detector solution. The detector solution is identical to detector solution A described earlier, and the prepared ozone detecting device is also identical to ozone detecting device A described earlier. Then, an ultraviolet absorber solution is prepared by dissolving 0.5 g of 2-(3, 5-di-t-pentyl-2-hydroxyphenyl)-2H-benzotriazole in 50 ml of acetone, and the above-mentioned ozone detecting device is dipped in this ultraviolet absorber solution for 10 sec so as to be impregnated with the ultraviolet absorber solution. After that, the ozone detecting device is pulled up from the ultraviolet absorber solution and dried in the same manner as described above, thereby forming ozone detecting device F.

A detector solution is prepared by dissolving 0.045 g of indigo carmine, 3.0 g of citric acid, and 12.5 g of glycerin in water to make 50 ml as a total amount, and an ozone detecting device is manufactured following the same procedures as described above by using this detector solution. The detector solution is identical to detector solution A described earlier, and the ozone detecting device is also identical to ozone detecting device A described earlier. Then, an ultraviolet absorber solution is prepared by dissolving 0.5 g of 2-(2-hydroxy-5-t-butylphenyl)-2H-benzotriazole in 50 ml of acetone, and the above-mentioned ozone detecting device is dipped in this ultraviolet absorber solution for 10 sec so as to be impregnated with the ultraviolet absorber solution. After that, the ozone detecting device is pulled up from the ultraviolet absorber solution and dried in the same manner as described above, thereby forming ozone detecting device G.

An ultraviolet exposure test (experiment) in which the ozone detecting devices A to G described above are irradiated with ultraviolet light is conducted. In this test, the influence of ultraviolet light was evaluated by using Artificial Sunlight XC-100AF available from SERIC with no UV filter attached. The incident angle of illuminating light to each of ozone detecting devices A to G was set at 20°, the distance from the lower end of the artificial sunlight to each of ozone detecting devices A to G was set at 110 cm, and each of ozone detecting devices A to G was set in a central portion where the intensity of the illuminating light is highest.

Figure 3:
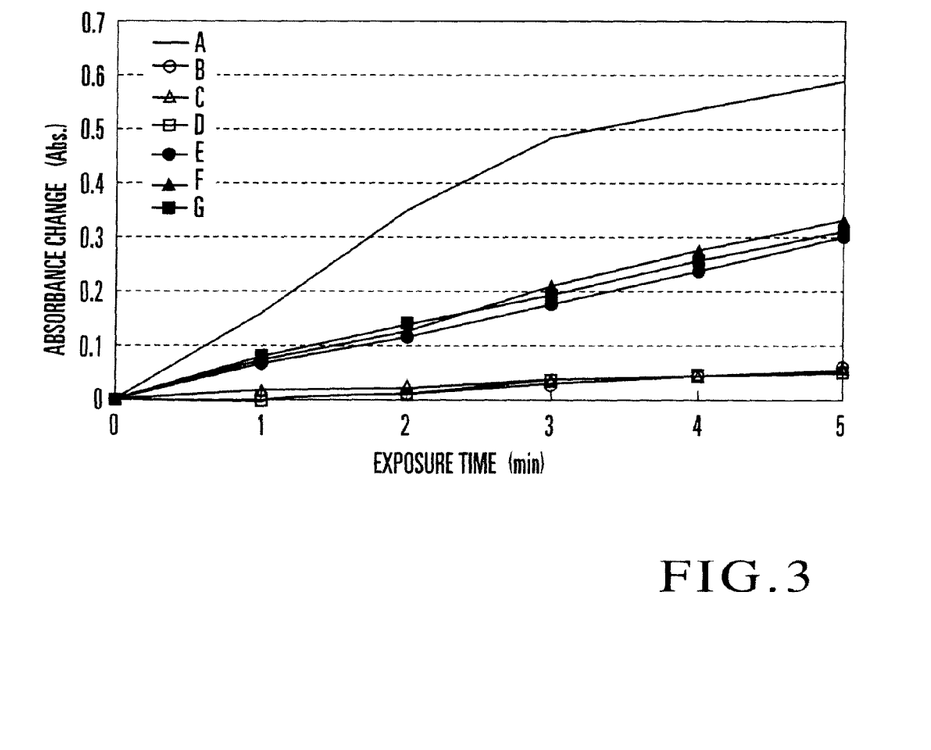
FIG. 3 is a graph showing the results of evaluation of the influence of ultraviolet light by using the change in absorbance at a wavelength of about 618 nm as an index, when ozone detecting devices A to G were irradiated with ultraviolet light minute by minute for 1 to 5 min, and the reflected light of each ozone detecting device was measured with a spectrophotometer whenever the device was irradiated.
Figure 4A:
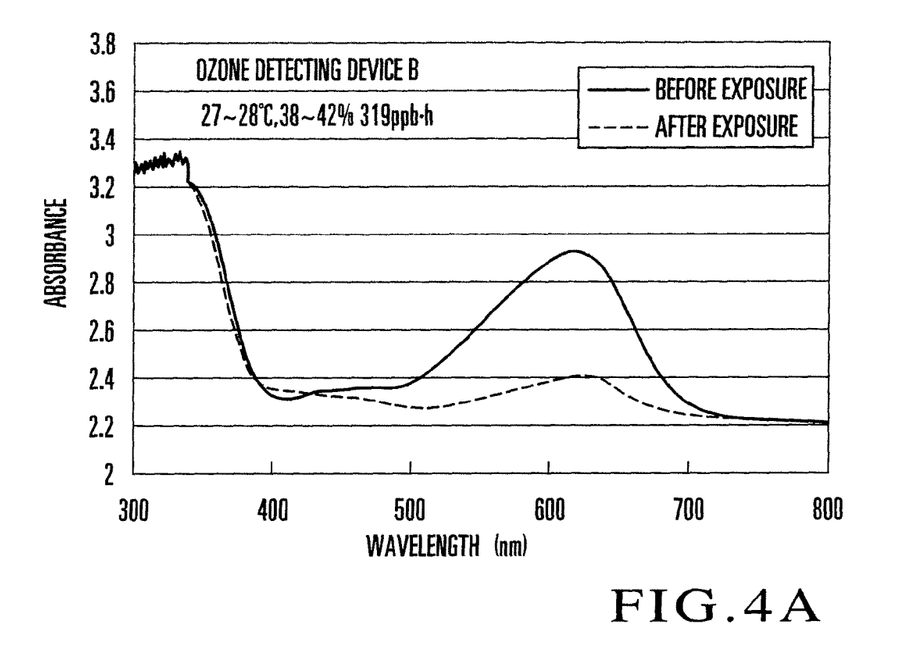
FIG. 4A is a graph showing the change in absorbance when detecting sheet B was exposed to a predetermined amount of ozone gas.
Figure 4B:
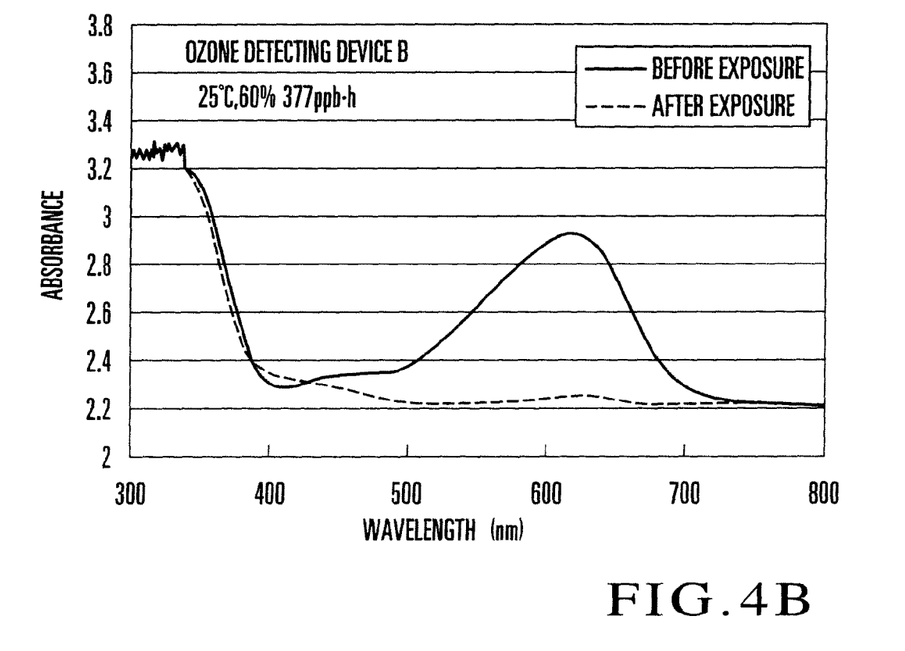
FIG. 4B is a graph showing the change in absorbance when detecting sheet B was exposed to a predetermined amount of ozone gas.
Figure 5A:
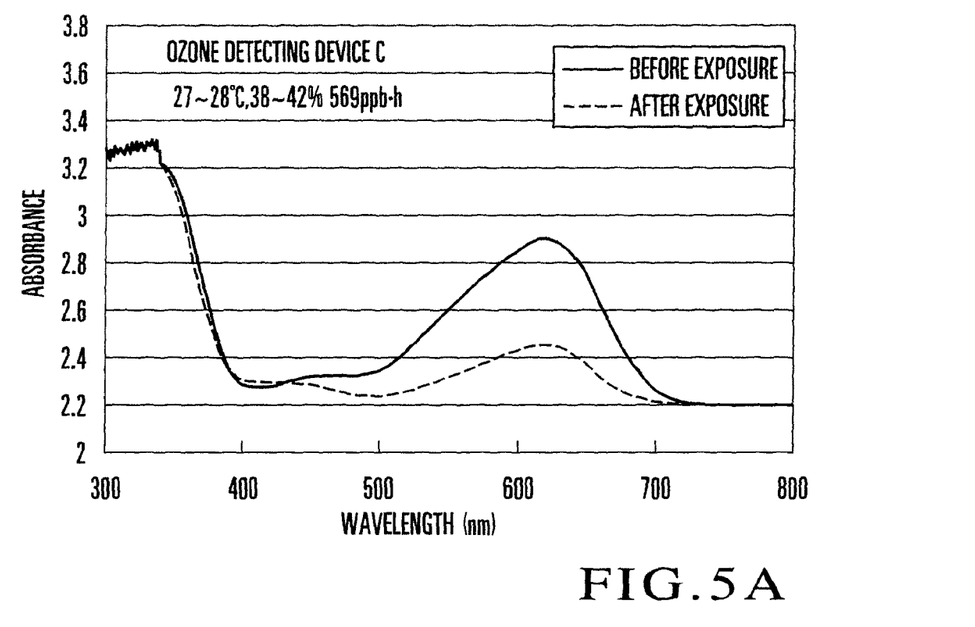
FIG. 5A is a graph showing the change in absorbance when ozone detecting sheet C was exposed to a predetermined amount of ozone gas.
Figure 5B:
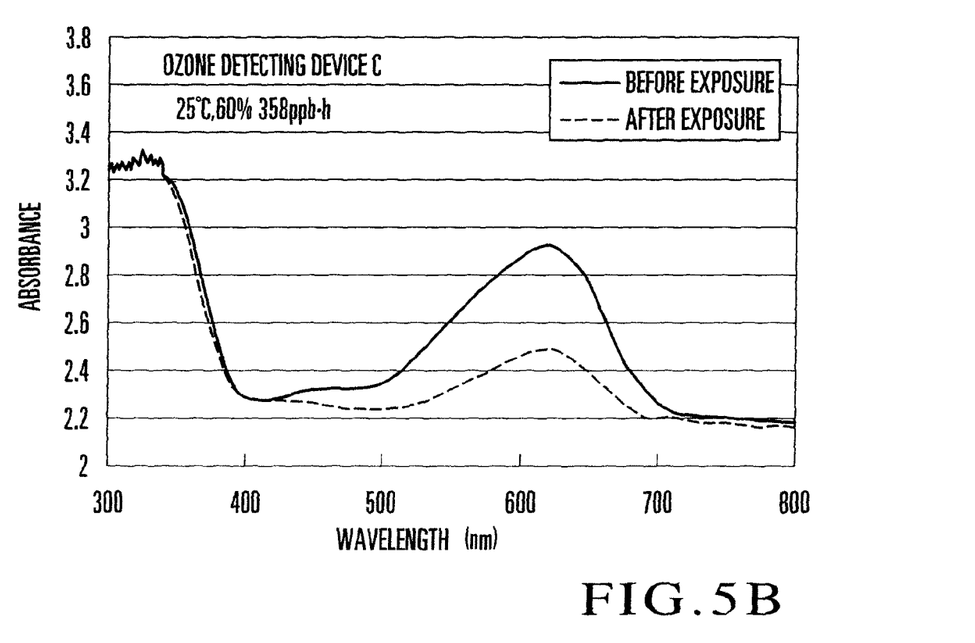
FIG. 5B is a graph showing the change in absorbance when ozone detecting sheet C was exposed to a predetermined amount of ozone gas.
Figure 6A:
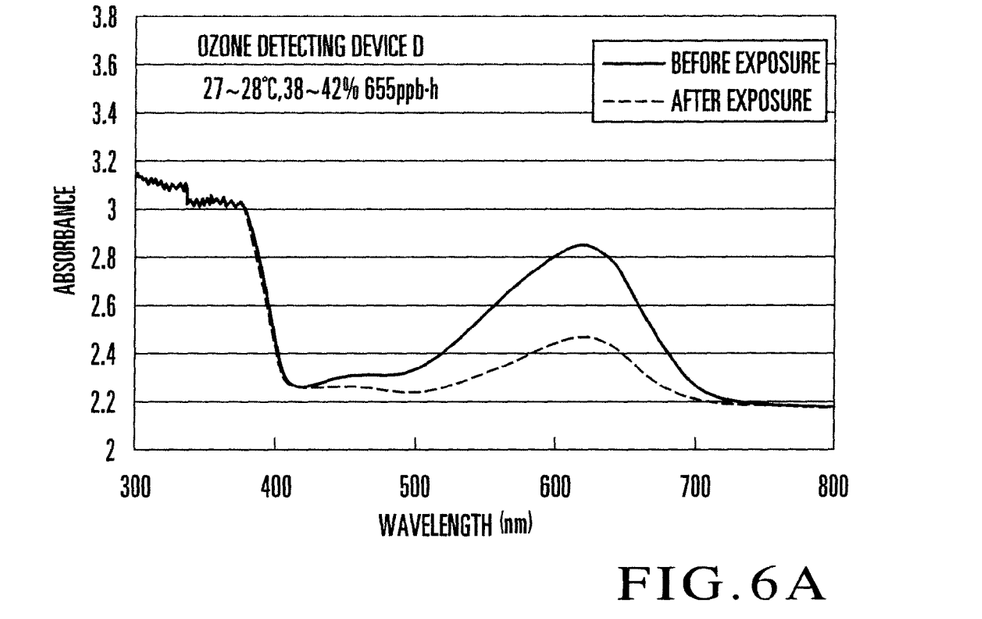
FIG. 6A is a graph showing the change in absorbance when ozone detecting sheet D was exposed to a predetermined amount of ozone gas.
Figure 6B:
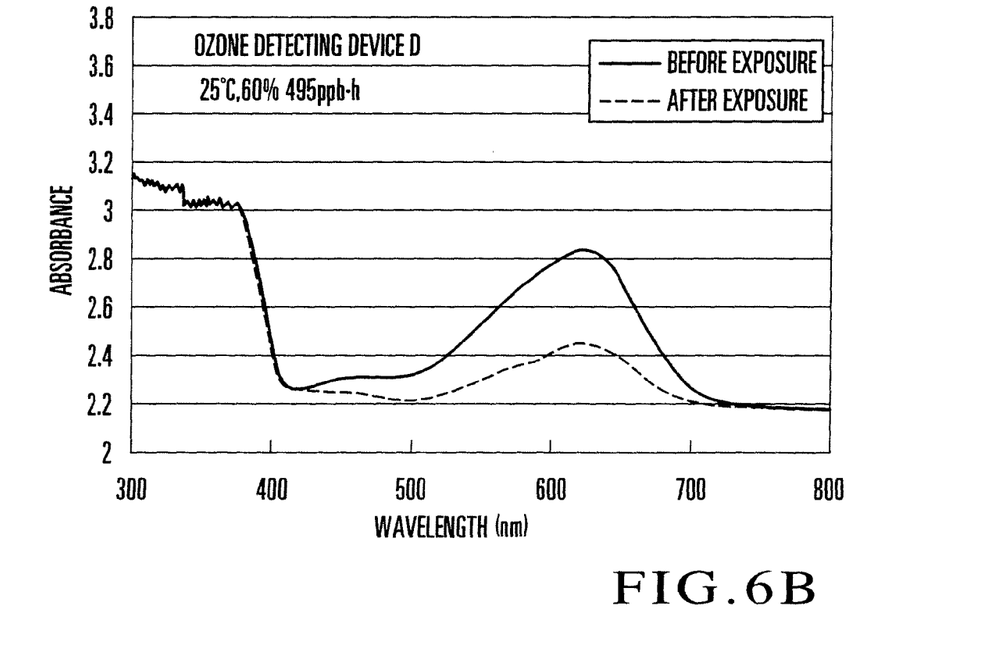
FIG. 6B is a graph showing the change in absorbance when ozone detecting sheet D was exposed to a predetermined amount of ozone gas.

Each of ozone detecting devices A to G described above was irradiated with ultraviolet light minute by minute for 1 to 5 min, and the reflected light from the ozone detecting device was measured with a spectrophotometer whenever the device was irradiated. The influence of ultraviolet light was evaluated by using the change in absorbance at a wavelength of about 618 nm as an index. FIG. 3 shows the results. Note that only the solid line indicates the result of ozone detecting device A, the hollow circles indicate the result of ozone detecting device B, the hollow triangles indicate the result of ozone detecting device C, the hollow squares indicate the result of ozone detecting device D, the solid circles indicate the result of ozone detecting device E, the solid triangles indicate the result of ozone detecting device F, and the solid squares indicate the result of ozone detecting device G.

As shown in FIG. 3, when compared to ozone detecting device A to which no ultraviolet absorber was added, the change in absorbance at a wavelength of 618 nm was small in any of ozone detecting devices B to G to which the ultraviolet absorbers were added. However, the influence of ultraviolet light was particularly reduced in ozone detecting devices B, C, and D among these ozone detecting devices to which the ultraviolet absorbers were added.

On a clear day in a season during which ultraviolet radiation is most intense, a maximum amount of ultraviolet radiation is presumably about 300 to 500 W·h/day. When ozone detecting device A to which no ultraviolet absorber was added was exposed to the sunshine, the absorbance at a wavelength of about 618 nm changed in proportion to the ultraviolet exposure amount, and decreased by about 0.6 when the amount of ultraviolet radiation was 200 W·h. This result almost matches the result when ozone detecting device A was irradiated minute by minute for 5 min in the exposure experiment using Artificial Sunlight XC-100AF (with no filter attached). Also, the absorbance at a wavelength of about 618 nm of ozone detecting device A changed in proportion to an ozone gas exposure amount, and decreased by about 0.7 when the device was exposed to 640 ppb·h (humidity 60%) of ozone gas.

From the foregoing, to suppress an error caused by the sunshine to 20% or less (0.14 or less as the absorbance change) even when an ozone detecting device is exposed to a possible maximum exposure amount of 300 W·h, the influence of ultraviolet light must be reduced to 15.6% on the basis of "200 W:0.6=300 W×x:0.14, x=0.156". When irradiation was performed minute by minute for 5 min in the ultraviolet exposure experiment using Artificial Sunlight XC-100AF (with no filter attached), the absorbance change of ozone detecting device A (containing no ultraviolet absorber) was 0.586, and those of ozone detecting devices B, C, and D were respectively 0.057, 0.047, and 0.057, i.e., 10% or less the absorbance change of ozone detecting device A. That is, ozone detecting devices B to D exhibit satisfactory ultraviolet absorbing ability.

By contrast, ozone detecting devices E, F, and G for comparison reduced the influence of ultraviolet light by about 50%, i.e., cannot achieve the necessary ultraviolet absorbing ability. These results demonstrate that to use a device as an ozone detecting device by suppressing the influence of ultraviolet light, it is necessary to use a water-soluble ultraviolet absorber having a hydrophilic group as in ozone detecting devices B to D.

When 2-hydroxy-4-methoxybenzophenone-5-sulfonic acid trihydrate, 2-hydroxy-4-methoxybenzophenone-5-sodium sulfonate, and ferulic acid are each dissolved in a solvent and the spectrum of transmitted light is analyzed, the ultraviolet absorbing power is not so high compared to those when using other ultraviolet absorbers insoluble in water described previously. For example, when equal amounts of 2-hydroxy-4-methoxybenzophenone-5-sulfonic acid trihydrate and 4-dodecyloxy-2-hydroxybenzophenone are added, the ultraviolet absorbing ability of 4-dodecyloxy-2-hydroxybenzophenone is 1.25 times that of 2-hydroxy-4-methoxybenzophenone-5-sulfonic acid trihydrate on the average in a wavelength region of 300 to 400 nm.

Although the addition amount of 2-hydroxy-4-methoxybenzophenone-5-sulfonic acid trihydrate is 0.8 g and that of 4-dodecyloxy-2-hydroxybenzophenone is 0.5 g, i.e., there is a difference between the addition amounts, it is impossible to explain why the large difference is produced between the changes in absorbance by ultraviolet radiation when they are applied to ozone detecting devices. Note that the ultraviolet absorbing ability of an ultraviolet absorber is proportional to the addition amount. When dissolved in a solvent, therefore, the absorbing ability of 0.8 g of 2-hydroxy-4-methoxybenzophenone-5-sulfonic acid trihydrate is about 1.3 times that of 0.5 g of 4-dodecyloxy-2-hydroxybenzophenone.

As shown in FIG. 3, the absorbance change of ozone detecting device E is about five times that of ozone detecting device B. Also, the absorbance change (Abs.) of ozone detecting device A to which no ultraviolet absorber was added is proportional to the ultraviolet exposure amount until a little over 0.3. This reveals that the ultraviolet exposure amount and absorbance change are proportional while a sufficient amount of the dye remains.

When 0.5 g or more of any of three types of water-insoluble ultraviolet absorbers, i.e., 4-dodecyloxy-2-hydroxybenzophenone, 2-(3,5-di-t-pentyl-2-hydroxyphenyl)-2H-benzotriazole, and 2-(2-hydroxy-5-t-butylphenyl)-2H-benzotriazole are added to 50 ml of acetone and a detecting device is manufactured using the solution, the ultraviolet absorber deposits in the form of powder on the surface of the ozone detecting device. By contrast, even when 9.0 g of 2-hydroxy-4-methoxybenzophenone-5-sulfonic acid trihydrate were added to 50 ml of water, 1.0 g of 2-hydroxy-4-methoxybenzophenone-5-sodium sulfonate was added to 50 ml of water, and 3.5 g of ferulic acid were added to 50 ml of acetone, and detecting devices were manufactured using the solutions, none of these ultraviolet absorbers deposited in the form of powder.

The reason for these phenomena is large differences between the values of water solubility. At 25° C., 2-hydroxy-4-methoxybenzophenone-5-sulfonic acid trihydrate dissolves in water in an amount of 25 wt %, 2-hydroxy-4-methoxybenzophenone-5-sodium sulfonate dissolves in water in an amount of more than 2.5 wt %, and ferulic acid dissolves in water in an amount of 0.05 wt %. By contrast, other ultraviolet absorbers are almost insoluble in water.

A water-insoluble ultraviolet absorber aggregates when a carrier impregnated with the solution is dried, and deposits in the form of powder on the surface from which the solvent has volatilized. This presumably forms a nonuniform distribution of the ultraviolet absorber, and makes it impossible to well achieve the ultraviolet absorbing effect. Also, even when the ultraviolet absorber does not deposit in the form of powder on the surface of the carrier, the concentration probably becomes nonuniform to make high ultraviolet absorbing ability impossible to obtain in a low-concentration portion.

When using an ultraviolet absorber having water solubility to some extent, however, glycerin carried by the carrier or water held by glycerin bonds to a hydrophilic group of the ultraviolet absorber molecule. Also, when the carrier is made of cellulose, a hydroxyl group of cellulose bonds to a hydrophilic group of the ultraviolet absorber molecule. When the carrier is dried, therefore, the ultraviolet absorber hardly aggregates and is uniformly held (carried) by the carrier. This perhaps achieves high ultraviolet absorbing ability.

Ferulic acid dissolves in water to about 0.05 wt %, and is also soluble in acetone. In the manufacture of ozone detecting device D, ferulic acid was dissolved in acetone and the solution was dispersed in ozone detecting device D in order to make the addition amount of ferulic acid larger than that soluble in water. This made it possible to achieve uniform dispersion and high ultraviolet absorbing ability. This demonstrates that even when adding an ultraviolet absorber in an amount larger than that soluble in water by the method of manufacturing ozone detecting device D described previously, the ultraviolet absorber can be uniformly held when dried if the water solubility is 0.05 wt % or more at 25° C.

In the manufacture of ozone detecting device D, an ozone detecting device containing no ultraviolet absorber was impregnated with acetone in which an ultraviolet absorber was dissolved, in order to make the addition amount of the ultraviolet absorber larger than that soluble in water. However, the solvent for dissolving the ultraviolet absorber need only be a solvent which does not quickly elute the constituent elements (the dye such as indigo carmine, the acidic substance such as citric acid, and the humectant such as glycerin) of the ozone detecting device containing no ultraviolet absorber, and in which the ultraviolet absorber is soluble. For example, ethyl acetate or the like can also be preferably used.

Generally, an ultraviolet absorber is used as it is added to a paint or resin or dissolved in a liquid such as oil as in cosmetics. Therefore, once an ultraviolet absorber is dissolved or uniformly dispersed in a solvent, a hydrophilic group contained in the ultraviolet absorber molecule is not important after that. In the ozone detecting device according to the present invention described above, however, the ultraviolet absorber must be dissolved in a solvent and uniformly dispersed after being dried. Accordingly, a hydrophilic group is an essential constituent element as described previously. This way of using an ultraviolet absorber largely differs from the general way of using an ultraviolet absorber, so the present invention cannot be easily analogized.

Examples of a water-soluble ultraviolet absorber other than the above-mentioned ultraviolet absorbers are p-aminobenzoic acid (water solubility 0.4 wt %) and phenyl salicylate (water solubility 0.05 wt %).

It is readily possible to analogize that even these ultraviolet absorbers can be uniformly held. These ultraviolet absorbers also have a benzene ring in the skeleton. Note that an index of the water solubility is 0.05 wt % or more of ferulic acid.

Although 3.5 g of citric acid were added to ozone detecting device C and ozone detecting device D, it was experimentally confirmed that almost the same results were obtained even when adding 2.0 g of acetic acid instead. It was also experimentally confirmed that the same results were obtained even when using ethyleneglycol or propyleneglycol instead of glycerin as the humectant. Furthermore, it was experimentally confirmed that even when using azo dyes (chalcone and Acid Alizarin Violet N), an anthraquinone dye (alizarin), annatto dye, it was possible to increase the resistance to ultraviolet light.

Note that as shown in FIGS. 3A, 3B, 4A, 4B, 5A, and 5B and Table 1 below, when ozone detecting devices B, C, and D were exposed to a predetermined amount of ozone gas, the absorbances well changed although the changes in absorbance were slightly different, indicating that these devices are usable as ozone detecting devices.

TABLE 1

| Sample | Temperature and humidity conditions | Total exposure amount (ppb · h) | Initial Abs |
|---|---|---|---|
| A (reference) | 27-28° C., 38-42% | 319 | 2.9453 |
| B | 27-28° C., 38-42% | 319 | 2.9362 |
| A (reference) | 25° C., 60% | 377 | 2.9404 |
| B | 25° C., 60% | 377 | 2.9129 |
| A (reference) | 27-28° C., 38-42% | 569 | 2.8983 |
| C | 27-28° C., 38-42% | 569 | 2.9059 |
| A (reference) | 25° C., 60% | 358 | 2.8607 |
| C | 25° C., 60% | 358 | 2.9179 |
| A (reference) | 27-28° C., 38-42% | 655 | 2.8926 |
| D | 27-28° C., 38-42% | 655 | 2.8437 |
| A (reference) | 25° C., 60% | 495 | 2.9119 |
| D | 25° C., 60% | 495 | 2.8254 |

| Sample | Abs after exposure | Abs change | Relative sensitivity |
|---|---|---|---|
| A (reference) | 2.5259 | 0.4194 | |
| B | 2.3997 | 0.5365 | 1.28 |
| A (reference) | 2.3755 | 0.5649 | |
| B | 2.2461 | 0.6668 | 1.18 |
| A (reference) | 2.2770 | 0.6213 | |
| C | 2.4697 | 0.4362 | 0.70 |
| A (reference) | 2.2680 | 0.5927 | |
| C | 2.4886 | 0.4293 | 0.72 |
| A (reference) | 2.2664 | 0.6262 | |
| D | 2.4969 | 0.3468 | 0.55 |
| A (reference) | 2.2675 | 0.6444 | |
| D | 2.4298 | 0.3956 | 0.61 |

INDUSTRIAL APPLICABILITY

The ozone detecting device of the present invention described above uses the ultraviolet absorber having an hydrophilic group, and the ultraviolet absorber uniformly distributes in the carrier without aggregating and absorbs ultraviolet light. Since this suppresses the influence of ultraviolet radiation on the dye carried by the carrier, the change of the dye caused by ultraviolet light is much smaller than the change (absorbance change) of the dye caused by ozone gas. Consequently, the ozone detecting device according to this embodiment can detect ozone gas even when exposed to ultraviolet light.

The conventional ozone detecting devices cannot be used outdoors because they are strongly influenced by ultraviolet light, and hence are limitedly used to detect ozone gas artificially generated indoors by, e.g., sterilization and deodorization in factories, kitchens, and hotel rooms. By contrast, the ozone detecting device of the present invention can be used outdoors because the influence of ultraviolet light is significantly reduced. In particular, photochemical smog often occurs at a high concentration on a clear day in summer, and the ultraviolet light amount inevitably increases on a day like this, so the conventional ozone detecting devices cannot be used. However, the present invention makes it possible to accurately detect ozone gas even in this environment. Also, the ozone detecting device according to the present invention can be preferably used to detect ozone generated by an apparatus that generates ozone by emitting ultraviolet light. Furthermore, the ozone detecting device according to the present invention can be easily carried by an individual because the device uses no electric power.

The invention claimed is:
1. An ozone detecting device comprising:
a carrier made of fibers;
a detector component carried by said carrier and containing at least a dye which changes color when reacting with ozone gas; and
an ultraviolet absorber carried by said carrier and having a hydrophilic group,
wherein said detector component contains an anthraquinone-based dye including a hydroxy group as said dye, and an alkaline substance.

2. An ozone detecting device comprising:

a carrier made of fibers;

a detector component carried by said carrier and containing at least a dye which changes color when reacting with ozone gas; and an ultraviolet absorber carried by said carrier and having a hydrophilic group, wherein said dye is an annatto dye including a polyene structure.

3. An ozone detecting device according to claim 1, wherein said dye is one of alizarin and Alizarin Red S.

4. An ozone detecting device according to claim 1 or 2, wherein said ultraviolet absorber includes a benzene ring in a skeleton.

5. An ozone detecting device according to claim 4, wherein said ultraviolet absorber dissolves in water at 25° C. in an amount of not less than 0.05 wt %.

6. An ozone detecting device according to claim 5, wherein said ultraviolet absorber is selected from the group consisting of 2-hydroxy-4-methoxybenzophenone-5-sulfonic acid, 2-hydroxy-4-methoxybenzophenone-5-sodium sulfonate, and ferulic acid.

7. An ozone detecting device according to claim 1, further comprising a humectant carried together with said dye by said carrier.

8. An ozone detecting device according to claim 2, wherein said humectant is selected from the group consisting of glycerin, ethyleneglycol, and propyleneglycol.

* * * * *

UNITED STATES PATENT AND TRADEMARK OFFICE
CERTIFICATE OF CORRECTION

PATENT NO. : 8,084,003 B2
APPLICATION NO. : 12/444845
DATED : December 27, 2011
INVENTOR(S) : Takashi Miwa et al.

It is certified that error appears in the above-identified patent and that said Letters Patent is hereby corrected as shown below:

In the Claims, Column 14, Claim 5, line 2, please delete "25° C." and insert -- 25° C --.

Signed and Sealed this
Thirteenth Day of November, 2012

David J. Kappos
*Director of the United States Patent and Trademark Office*